United States Patent [19]

Dellaria et al.

[11] Patent Number: 5,681,842
[45] Date of Patent: Oct. 28, 1997

[54] PROSTAGLANDIN SYNTHASE-2 INHIBITORS

[75] Inventors: Joseph F. Dellaria, Lindenhurst; Todd H. Gane, Waukegan, both of Ill.

[73] Assignee: Abbott Laboratories, Abbott Park, Ill.

[21] Appl. No.: 744,906

[22] Filed: Nov. 8, 1996

[51] Int. Cl.$^6$ .............. C07D 277/62; C07D 263/56; C07D 333/54; C07D 235/08

[52] U.S. Cl. .............. 514/367; 514/375; 514/443; 514/394; 514/465; 514/464; 514/469; 514/415; 548/178; 548/217; 548/304.4; 548/469; 549/471; 549/437; 549/51

[58] Field of Search .............. 514/367, 375, 514/443, 394, 465, 464, 469, 415; 548/178, 217, 304.4, 469; 549/471, 437, 51

[56] References Cited

U.S. PATENT DOCUMENTS

| | | | |
|---|---|---|---|
| 3,840,597 | 10/1974 | Moore et al. | 260/556 F |
| 4,375,479 | 3/1983 | Schroeder | 424/321 |
| 4,866,091 | 9/1989 | Matsuo et al. | 514/471 |

FOREIGN PATENT DOCUMENTS

| | | |
|---|---|---|
| 9413635 | 6/1994 | WIPO . |
| 9420480 | 9/1994 | WIPO . |

OTHER PUBLICATIONS

Mitchell et al; Cyclooxygenase–2: Regulation and Relevance in Inflammation; Biochemical Pharmacology. vol. 50 No. 10 pp. 1535–1542, 1995.

Battistini et al; Cox–1 and Cox–2:"Toward the Development of More Selective Nsaids" (1994) Drug News and Perspectives, 7(8), 501–512.

DeWitt et al; The Differential Susceptibility of Prostaglandin Endoperoxide H Synthases–1 and –2 to Nonsteroidal Anti-Inflammatory Drugs: Aspirin Derivatives as Selective Inhibitors; Med Chem Res (1995) 5:325–343.

*Primary Examiner*—José G. Dees
*Assistant Examiner*—Laura R. Cross

[57] ABSTRACT

The present invention provides a compound of the formula:

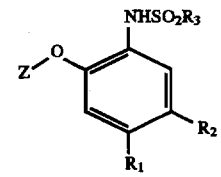

such compounds are useful for inhibiting prostaglandin synthesis. Pharmaceutical compositions and methods for inhibiting prostaglandin synthesis are also disclosed.

10 Claims, No Drawings

PROSTAGLANDIN SYNTHASE-2 INHIBITORS

TECHNICAL FIELD

This invention relates to novel compounds having activity to inhibit prostaglandin biosynthesis, to pharmaceutical compositions comprising these compounds and to a medical method of treatment. More particularly, this invention concerns fused carbocyclic or fused heterocyclic containing derivatives of sulfonamides which inhibit prostaglandin biosynthesis, particularly the induced prostaglandin endoperoxide H synthase (PGHS-2, but also known as cyclooxygenase-2 (COX-2)), to pharmaceutical compositions comprising these compounds and to a method of inhibiting prostaglandin biosynthesis.

BACKGROUND OF THE INVENTION

The prostaglandins are extremely potent substances which produce a wide variety of biological effects, often in the nanomolar to picomolar concentration range. The discovery of two forms of prostaglandin endoperoxide H synthase-1 and -2 (PGHS-1 and PGHS-2) that catalyze the oxidation of arachidonic acid leading to prostaglandin biosynthesis has resulted in renewed research to delineate the role of these two isozymes in physiology and pathophysiology. These isozymes have been shown to have different gene regulation and represent distinctly different prostaglandin biosynthesis pathways. The PGHS-1 pathway is expressed constitutively in most cell types. It responds to produce prostaglandins that regulate acute events in vascular homeostasis and also has a role in maintaining normal stomach and renal function. The newly discovery PGHS-2 pathway involves an induction mechanism which has been linked to inflammation, mitogenesis and ovulation phenomena.

Prostaglandin inhibitors provide therapy for pain, fever and inflammation for example, in the treatment of rheumatoid arthritis and osteoarthritis. The non-steroidal antiinflammatory drugs (NSAIDs) such as ibuprofen, naproxen and fenamates inhibit both isozymes, i.e. prostaglandin endoperoxide H synthase 1 (PGHS-1) and prostaglandin endoperoxide H synthase 2 (PGHS-2). Inhibition of the constitutive enzyme PGHS-1 results in gastrointestinal side effects including ulcers and bleeding and incidence of renal problems with chronic therapy.

Inhibitors of the induced isozyme PGHS-2 are proposed to provide antiinflammatory activity without the side effects of PGHS-1 inhibitors. A general review of the current knowledge of PGHS-1 and PGHS-2 isozyme properties and a summary of inhibitors and their activity has been reviewed by: (1) Battistini, B.; Botting, R.; Bakhle, Y. S., "COX-1 and COX-2: Toward the Development of More Selective NSAIDs", Drug News and Perspectives, 7(8): 501–512 (1994); (2) DeWitt, D. L.; Bhattacharyya, D.; Lecomte, M.; Smith, W. L., "The Differential Susceptibility of Prostaglandin Endoperoxide H Synthases-1 and -2 to Nonsteroidal Anti-inflammatory Drugs: Aspirin Derivatives as Selective Inhibitors", Med. Chem. Res. 5(5): 325–343 (1995); and (3) Mitchell, J. A.; Larkin, S.; Williams, T. J., Cyclooxygenase-2: Regulation and Relevance in Inflammation. Biochem. Pharm. 50(10): 1535–1542 (1995).

The current invention provides novel fused carbocyclic or fused heterocyclic containing derivatives of sulfonamides with unexpected preferential inhibitory activity against the induced PGHS-2 isozyme versus PGHS-1.

SUMMARY OF THE INVENTION

The present invention provides novel naphthyl and fused heterocycle containing derivatives of sulfonamide compounds with unexpected preferential inhibitory activity against induced PGHS-2 isozyme versus PGHS-1.

In its principal embodiment, the present invention provides a compound of the formula:

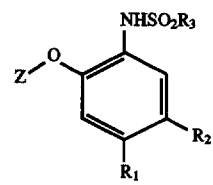

I wherein Z is selected from the group consisting of (a) naphthyl; (b) substituted naphthyl wherein the hydrogen atom attached to one to four of the carbon atoms is replaced with a substituent independently selected from $R_4$ wherein $R_4$ is —F, —CN, —Cl, or —CF$_3$; (c) benzimidazol-5-yl; (d) substituted benzimidazol-5-yl wherein the hydrogen atom attached to one to four of the carbon atoms is replaced with a substituent independently selected from $R_4$ wherein $R_4$ is as defined above; (e) benzthiazol-6-yl; (f) substituted benzthiazol-6-yl wherein the hydrogen atom attached to one to four of the carbon atoms is replaced with a substituent independently selected from $R_4$ wherein $R_4$ is as defined above; (g) benzoxazol-5-yl; (h) substituted benzoxazol-5-yl wherein the hydrogen atom attached to one to four of the carbon atoms is replaced with a substituent independently selected from $R_4$ wherein $R_4$ is as defined above; (i) benzoxazol-6-yl; (j) substituted benzoxazol-6-yl wherein the hydrogen atom attached to one to four of the carbon atoms is replaced with a substituent independently selected from $R_4$ wherein $R_4$ is as defined above; (k) benzthiophen-5-yl; (l) substituted benzthiophen-5-yl wherein the hydrogen atom attached to one to four of the carbon atoms is replaced with a substituent independently selected from $R_4$ wherein $R_4$ is as defined above; (m) benzthiophen-6-yl; (n) substituted benzthiophen-6-yl wherein the hydrogen atom attached to one to four of the carbon atoms is replaced with a substituent independently selected from $R_4$ wherein $R_4$ is as defined above; (o) benzimidazol-5-yl wherein the hydrogen atom attached to the nitrogen atom is optionally substituted with lower alkyl; (p) substituted benzimidazol-5-yl wherein the hydrogen atom attached to the nitrogen atom is optionally substituted with lower alkyl and the hydrogen atom attached to one to four of the carbon atoms is replaced with a substituent independently selected from $R_4$ wherein $R_4$ is as defined above; (q) benzimidazol-6-yl wherein the hydrogen atom attached to the nitrogen atom is optionally substituted with lower alkyl; (r) substituted benzimidazol-6-yl wherein the hydrogen atom attached to the nitrogen atom is optionally substituted with lower alkyl and the hydrogen atom attached to one to four of the carbon ring atoms is replaced with a substituent independently selected from $R_4$ wherein $R_4$ is as defined above; (s) 1,3-benzodioxol-5-yl; (t) substituted 1,3-benzodioxol-5-yl wherein the hydrogen atom attached to one or two of the carbon ring atoms is replaced with a substituent independently selected from $R_4$ wherein $R_4$ is as defined above; (u) benzofur-5yl; (v) substituted benzofur-5-yl wherein the hydrogen atom attached to one to four of the carbon ring atoms is replaced with a substituent independently selected from $R_4$ wherein $R_4$ is as defined above; (w) benzofur-6-yl; (x) substituted benzofur-6-yl wherein the hydrogen atom attached to one to four of the carbon ring atoms is replaced with a substituent independently selected from $R_4$ wherein $R_4$ is as defined above; (y) indol-5-yl wherein the hydrogen atom attached to the nitrogen atom is optionally substituted with lower alkyl; (z) substituted indol-5-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above; (aa) indol-6-yl wherein the hydrogen atom attached to the nitrogen atom is optionally substituted with lower alkyl; and (bb) substituted indol-6-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;

$R_1$ is selected from the group consisting of —$NO_2$, —CN, —Cl, and $CF_3$;

$R_2$ is —H or $R_1$ and $R_2$ taken together with the atoms to which they are attached define a 5-, 6- or 7-membered saturated carbocyclic or saturated heterocyclic ring having a single heteroatom selected from oxygen, nitrogen or sulfur wherein the carbocyclic or heterocyclic ring is unsubstituted or substituted with one or two substituents selected from the group consisting of oxo, alkyl and hydroxyl; and $R_3$ is selected from the group consisting of lower alkyl and $CH_nF_{(3-n)}$ wherein n is 0, 1, 2 or 3;

or a pharmaceutically acceptable salt or prodrug thereof.

In another embodiment, the present invention also provides pharmaceutical compositions useful for inhibiting prostaglandin biosynthesis comprising a therapeutically effective amount of a compound of the invention in combination with a pharmaceutically acceptable carrier.

In yet another embodiment, the present invention provides a method of inhibiting prostaglandin biosynthesis in a host mammal comprising administering to a mammal in need of such treatment a therapeutically effective amount of a compound of the invention.

DETAILED DESCRIPTION OF THE INVENTION

As used throughout this specification and the appended claims, the following terms have the meanings specified.

The term "alkanoyl" as used herein refers to $R_5C(O)$— wherein $R_5$ is a lower alkyl group.

The term "alkoxy" as used herein refers to $R_6O$— wherein $R_6$ is a lower alkyl group.

The term "alkoxycarbonyl" as used herein refers to $R_7C(O)$— wherein $R_7$ is an alkoxy group.

The term "alkyl" as used herein refers to a monovalent group derived from a straight or branched chain saturated $C_1$–$C_{12}$ hydrocarbon by the removal of a single hydrogen atom.

The term "alkylamino" as used herein refers to —$NHR_8$ wherein $R_8$ is a lower alkyl group.

The term "aminocarbonyl" as used herein refers to —$C(O)NH_2$.

The term "aroyl" as used herein refers to $R_9C(O)$— wherein $R_9$ is an aryl group.

The term "aryl" as used herein refers to a mono- or bicyclic carbocyclic ring system comprising 6 to 12 carbon atoms and having one or two aromatic rings including, but not limited to, phenyl, naphthyl, tetrahydronaphthyl, indanyl, indenyl and the like. Aryl groups can be unsubstituted or substituted with one, two, three or four substituents independently selected from lower alkyl, halo, haloalkyl, haloalkoxy, alkoxy, alkoxycarbonyl, thioalkoxy, amino, alkylamino, dialkylamino, aminocarbonyl, mercapto, nitro, carboxaldehyde, carboxy and hydroxy.

The term "dialkylamino" as used herein refers to —$NR_{10}R_{11}$ wherein $R_{10}$ and $R_{11}$ are independently selected from lower alkyl groups.

The term "halo" as "halogen" as used herein refers to —Cl, —F, —Br, or —I.

The term "haloalkyl" as used herein refers to a lower alkyl group in which one or more hydrogen atoms are replaced by halogen, for example, chloromethyl, chloroethyl, trifluoromethyl and the like.

The term "haloalkoxy" as used herein refers to $R_{12}O$— wherein $R_{12}$ is a haloalkyl group.

The term "heterocyclic" or "heterocycle" or "heterocyclic ring" as used herein refers to a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; and two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The nitrogen heteroatoms can be optionally quaternized.

Heterocyclics can be unsubstituted or substituted with one, two, three or four substituents independently selected from the group consisting of hydroxy, halo, oxo (=O), alkoxy, haloalkyl, and lower alkyl. In addition, nitrogen containing heterocycles can be N-protected.

The term lower alkyl as used herein refers to a monovalent group derived from a straight or branched chain saturated $C_1$–$C_8$ hydrocarbon by the removal of a single hydrogen atom. Lower alkyl groups are exemplified by methyl, ethyl, n- and iso-propyl, n-, sec-, iso- and tert-butyl, and the like.

The term "thioalkoxy" as used herein refers to $R_{10}S$- wherein $R_{10}$ is a lower alkyl group.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

In its principal embodiment, the present invention provides a compound having the formula:

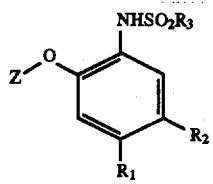

wherein

Z is selected from the group consisting of:
(a) naphthyl;
(b) substituted naphthyl wherein the hydrogen atom attached to one to four of the carbon atoms is replaced with a substituent independently selected from $R_4$ wherein $R_4$ is —F, —CN, —Cl, or —$CF_3$;
(c) benzthiazol-5-yl;
(d) substituted benzthiazol-5-yl wherein the hydrogen atom attached to one to four of the carbon atoms is replaced with a substituent independently selected from $R_4$ wherein $R_4$ is as defined above;
(e) benzthiazol-6-yl;
(f) substituted benzthiazol-6-yl wherein the hydrogen atom attached to one to four of the carbon atoms is replaced with a substituent independently selected from $R_4$ wherein $R_4$ is as defined above;
(g) benzoxazol-5-yl;
(h) substituted benzoxazol-5-yl wherein the hydrogen atom attached to one to four of the carbon atoms is replaced with a substituent independently selected from $R_4$ wherein $R_4$ is as defined above;
(i) benzoxazol-6-yl;
(j) substituted benzoxazol-6-yl wherein the hydrogen atom attached to one to four of the carbon atoms is replaced with a substituent independently selected from $R_4$ wherein $R_4$ is as defined above;
(k) benzthiophen-5-yl;
(l) substituted benzthiophen-5-yl wherein the hydrogen atom attached to one to four of the carbon atoms is replaced with a substituent independently selected from $R_4$ wherein $R_4$ is as defined above;
(m) benzthiophen-6-yl;
(n) substituted benzthiophen-6-yl wherein the hydrogen atom attached to one to four of the carbon atoms is replaced with a substituent independently selected from $R_4$ wherein $R_4$ is as defined above;
(o) benzimidazol-5-yl wherein the hydrogen atom attached to the nitrogen atom is optionally substituted with lower alkyl;
(p) substituted benzimidazol-5-yl wherein the hydrogen atom attached to the nitrogen atom is optionally substituted with lower alkyl and the hydrogen atom attached to one to four of the carbon atoms is replaced with a substituent independently selected from $R_4$ wherein $R_4$ is as defined above;
(q) benzimidazol-6-yl wherein the hydrogen atom attached to the nitrogen atom is optionally substituted with lower alkyl;
(r) substituted benzimidazol-6-yl wherein the hydrogen atom attached to the nitrogen atom is optionally substituted with lower alkyl and the hydrogen atom attached to one to four of the carbon ring atoms is replaced with a substituent independently selected from $R_4$ wherein $R_4$ is as defined above;
(s) 1,3-benzodioxol-5-yl;
(t) substituted 1,3-benzodioxol-5-yl wherein the hydrogen atom attached to one or two of the carbon ring atoms is replaced with a substituent independently selected from $R_4$ wherein $R_4$ is as defined above;
(u) benzofur-5-yl;
(v) substituted benzofur-5-yl wherein the hydrogen atom attached to one to four of the carbon ring atoms is replaced with a substituent independently selected from $R_4$ wherein $R_4$ is as defined above;
(w) benzofur-6-yl;
(x) substituted benzofur-6-yl wherein the hydrogen atom attached to one to four of the carbon ring atoms is replaced with a substituent independently selected from $R_4$ wherein $R_4$ is as defined above;
(y) indol-5-yl wherein the hydrogen atom attached to the nitrogen atom is optionally substituted with lower alkyl;
(z) substituted indol-5-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;
(aa) indol-6-yl wherein the hydrogen atom attached to the nitrogen atom is optionally substituted with lower alkyl; and
(bb) substituted indol-6-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;

$R_1$ is selected from the group consisting of —$NO_2$, —CN, —Cl, and $CF_3$;

$R_2$ is —H or $R_1$ and $R_2$ taken together with the atoms to which they are attached define a 5-, 6- or 7-membered saturated carbocyclic or saturated heterocyclic ring having a single heteroatom selected from oxygen, nitrogen or sulfur wherein the carbocyclic or heterocyclic ring is unsubstituted or substituted with one or two substituents selected from the group consisting of oxo, alkyl and hydroxyl; and $R_3$ is selected from the group consisting of lower alkyl and $CH_nF_{(3-n)}$ wherein n is 0, 1,2 or 3;

or a pharmaceutically acceptable salt or prodrug thereof.

Preferred compounds of the invention are compounds of formula I wherein Z and $R_3$ are as defined above and $R_1$ and $R_2$ taken together with the atoms to which they are attached define a 5-membered saturated carbocyclic ring substituted with oxo.

More preferred compounds of the invention are compounds of formula I wherein Z is as defined above, $R_1$ is —$NO_2$, $R_2$ is —H and $R_3$ is $CH_3$.

Even more preferred compounds of the invention are compounds of formula I wherein Z is (a) naphthyl; (b) substituted naphthyl wherein the hydrogen atom attached to one to four of the carbon atoms is replaced with a substituent independently selected from $R_4$ wherein $R_4$ is as defined above; (c) benzthiazol-6-yl; (d) substituted benzthiazol-6-yl wherein the hydrogen atom attached to one to four of the carbon atoms is replaced with a substituent independently selected from $R_4$ wherein $R_4$ is as defined above; (e) benzthiophen-5-yl; (f) substituted benzthiophen-5-yl wherein the hydrogen atom attached to one to four of the carbon atoms is replaced with a substituent independently selected from $R_4$ wherein $R_4$ is as defined above; (g) 1,3-benzodioxol-6-yl; (h) substituted 1,3-benzodioxol-6-yl wherein the hydrogen atom attached to one to four of the carbon atoms is replaced with a substituent independently selected from $R_4$ wherein $R_4$ is as defined above; $R_1$ is —$NO_2$, $R_2$ is —H; and $R_3$ is —$CH_3$.

Even more preferred compounds of formula I are:

N-(4-Nitro-2-(naphth-2'-yloxy)phenyl) methanesulfonamide;

N-(4-Nitro-2-(6'-fluoronaphth-2'-yloxy)phenyl) methanesulfonamide;

N-(4-Nitro-2-(benzothiophen-5'-yloxy)phenyl) methanesulfonamide;

N-(4-Nitro-2-(benzothiazol-6'-yloxy)phenyl) methanesulfonamide; and

N-(4-Nitro-2-(1,3-benzodioxol-5'-yloxy)phenyl) methanesulfonamide or a pharmaceutically acceptable salt or prodrug thereof.

By pharmaceutically acceptable salt it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 66: 1–19 (1977). The salts can be prepared in situ during the final isolation and purification of the compounds of the invention, or separately by reacting the free base function with a suitable organic acid. Representative acid addition salts dodecylsulfate, ethanesulfonate, fumarate, glucoheptonate, glycerophosphate, hemisulfate, include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used throughout this specification and the appended claims, the term "metabolically clearable group" denotes a moiety which is readily cleaved in vivo from the compound bearing it, which compound after cleavage remains or becomes pharmacologically active. Metabolically clearable groups form a class of groups reactive with the aminosulfonyl group of the compounds of this invention. Such metabolically cleavable groups are well known to those of ordinary skill in the art and include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethylsilyl), monoesters formed with dicarboxylic acids (such as succinyl) and the like.

Because of the ease with which the metabolically clearable groups of the compounds of this invention are cleaved in vivo, the compounds bearing such groups act as prodrugs of other prostaglandin biosynthesis inhibitors. The compounds bearing the metabolically clearable groups have the advantage that they may exhibit improved bioavailability as a result of enhanced solubility and/or rate of absorption conferred upon the parent compound by virture of the presence of the metabolically cleavable group. A thorough discussion of prodrugs is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the invention are selective inhibitors of PGHS-2. As PGHS-2 inhibitors, these compounds are useful in the treatment of conditions which are mediated by PGHS-2 activity. More particularly, these compounds are useful for treating or modulating pathological conditions in mammals which are associated with the production of prostaglandins by PGHS-2. Thus, the compound is useful as an anti-inflammatory agent for treating both acute inflammatory conditions (such as those resulting from infection) and chronic inflammatory conditions (such as those resulting from asthma, arthritis and inflammatory bowel disease). It is also useful as an analgesic and anti-pyretic agent (i.e. for reducing pain and fever). Further uses are for the prevention of cardiovascular disease, the prevention of bone resorption and for the reduction of colon cancer.

Prostaglandin Inhibition Analysis

I. Methodologies a. Recombinant Human PGHS-1 and PGHS-2 Enzyme Assays:

A compound of the invention dissolved in DMSO (3.3% v/v) was preincubated with microsomes from recombinant human PGHS-1 or PGHS-2 expressed in the baculovirus/Sf9 cell system (Gierse, J. K., Hauser, S. D., Greely, D. P., Koboldt, C., Rangwala, S., H., Isakson, P. C., and Seibert, K. "Expression and selective inhibition of the constitutive and inducible forms of cyclooxygenase", *Biochem J*. 305:479 (1995)), together with the cofactors phenol (2 mM) and hematin (1 µM) for 60 minutes prior to the addition of 10 µM arachidonic acid. The reaction was allowed to run for 2.5 minutes at room temperature prior to quenching with HCl and neutralization with NaOH. $PGE_2$ production in the presence and absence of the drug was determined by EIA analysis.

b. EIA Determination of Prostaglandins:

EIA reagents for prostaglandin determination were purchased from Perseptive Diagnostics, Cambridge, Mass. $PGE_2$ levels in lavage fluids were determined after the samples were dried under nitrogen and reconstituted with assay buffer. $PGE_2$ levels in enzyme assays or cell culture media were measured against standards prepared in the same milieu. The immunoassays were conducted as recommended by the manufacturer. The EIA was conducted in 96 well microtiter plates (Nunc Roskilde, Denmark) and optical density measured using a microplate reader (Vmax, Molecular Devices Corp., Menlo Park, Calif.).

c. Carrageenan Induced Pleurisy Test (CIP):

Inhibition of carrageenan induced pleurisy in rats was determined essentially as described by F. B. De Brito, (Pleurisy and Pouch Models of Acute Inflammation in *Pharmalogical Methods in the Control of Inflammation*, Eds, J. Y. Chang and A. J. Lewis, Alan Liss Inc., New York: 173–194, 1989) and Vinegar et al. ("Quantitative studies of the pathway to acute carrageenan inflammation", *Fed. Proc.*, 35:2447–2456 (1976)). Briefly, eight Sprague-Dawley rats were orally dosed with 10 mg/kg of a compound of the invention 30 minutes prior to intrapleural injection of 2% lambda carrageenan (Sigma Chemical Co., St. Louis Mo.). Four hours after carrageenan injection, the animals were euthanized and their pleural cavities lavaged with ice cold saline. The lavage fluid was then added to two volumes of ice cold methanol (final methanol concentration 66%) to lyse cells and precipitate protein. Prostaglandin levels in the methanol/lavage fluid were then determined by EIA.

II. In vitro Assay Results

When tested in the recombinant human PGHS-1 and PGHS-2 enzyme assays as described above, all representative compounds were shown to be potent inhibitors of recombinant human PGHS-2, with compound 5 being most potent. (Please see Table 1). Furthermore, all representative compounds were shown to be more selective inhibitors of recombinant human PGHS-2 than recombinant human PGHS-1.

TABLE 1

In Vitro Inhibitory Potencies Against Human Recombinant PGHS-1 and PGHS-2

| Example | RHuPGHS-2 (% I @ 100 nM) | RHuPGHS-1 (% I @ 100µM) |
|---|---|---|
| 1 | 65% | 47% |
| 2 | 56% | 26% |
| 3 | 59% | 89% |
| 4 | 43% | 31% |
| 5 | 77% | 89% |

III. In vivo Results

When tested in the carrageenan induced pleurisy assay, the compounds of Examples 2, 3, 4, and 5 were shown to inhibit prostaglandin production in the pleural cavity by 20, 48, 66 and 36% respectively.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The methanesulfonamide compounds of the invention can be prepared as shown in Schemes 1 and 2. As outlined in Scheme 1, compound I, (which is commercially available) is first protected with a t-butyldimethylsilyl group under standard reaction conditions. The resulting silyl ether (II) is convened to the bis(sulfonamide) by treatment with two equivalents of a base, such as sodium hydride, and two equivalents of alkylsulfonyl chloride or fluorinated alkylsulfonyl chloride in a solvent such as dimethylformamide. Deprotection of the t-butyldimethylsilyl group occurs concomitantly during the quenching of the sulfonylation reaction to provide the bis(sulfonylamino)phenol (III). Mono-deprotection is achieved by exposing compound III to a refluxing solution of aqueous ethanol and an alkali metal hydroxide such as lithium hydroxide. The resulting sulfonylaminophenol (IV), is convened to a compound of the invention by heating in a solvent, such as dimethylformamide, in the presence of an alkali metal salt, such as potassium carbonate, and a copper halogen salt, such as copper iodide, and a compound Z of the invention which is halogenated with bromine or iodine.

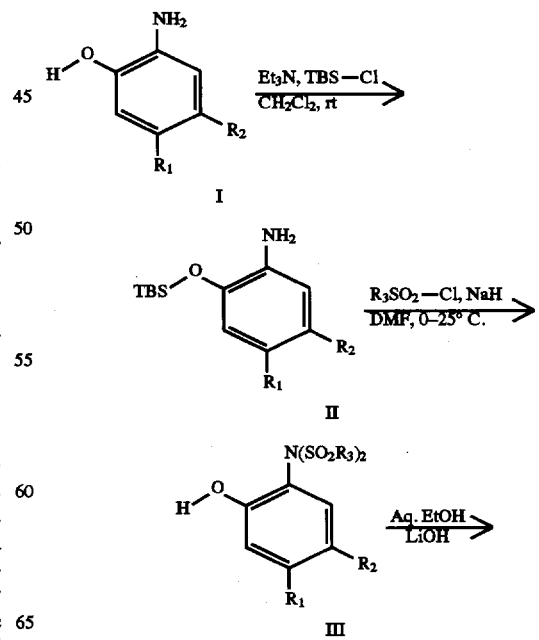

Scheme 1 -continued

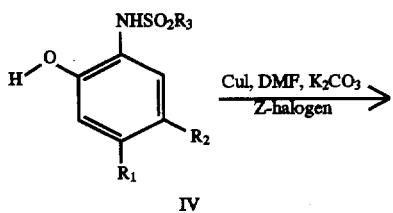

Alternatively, in Scheme 2, commercially available starting compound V is converted to the corresponding methanesulfonamide by treatment with a base, such as sodium hydride, and alkylsulfonyl chloride or fluorinated alkylsulfonyl chloride in a solvent such as dimethylformamide. The resulting (sulfonylamino)arylbromide (VI), is convened to a compound of the invention by heating in a solvent, in the presence of an alkali metal salt, and a copper halogen salt, (as described in Scheme 1), and a compound Z of the invention substituted with —OH.

Scheme 2

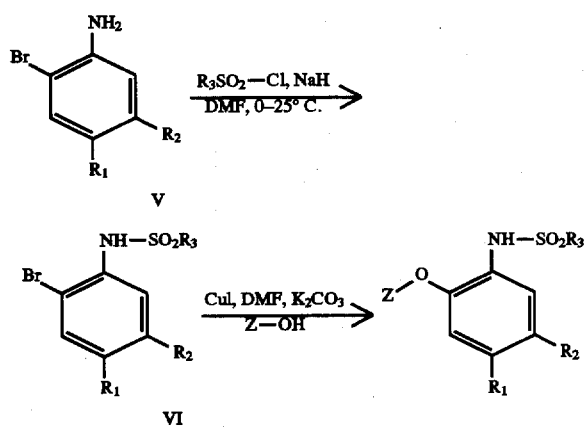

Trifluoromethanesulfonamide compounds may be prepared according to Scheme 3 below. As shown in Scheme 3, a methanesulfonamide compound of the invention is hydrolyzed by refluxing in a strong protic acid such as sulfuric acid in the presence of water and acetic acid. The resulting aniline intermediate (VII) is then converted to a bis (trifluorosulfonamide) intermediate (VIII) by treatment with trifluoromethanesulfonic anhydride at a temperature from about −23° C. to about 0° C. in the presence of a hindered amine such as lutidine and a solvent such as dichloromethane. Intermediate VIII is then monodeprotected by exposure to an aqueous solution of an alkali metal hydroxide, such as sodium hydroxide, in a solvent such as THF to yield a trifluoromethanesulfonamide compound of the invention.

Scheme 3

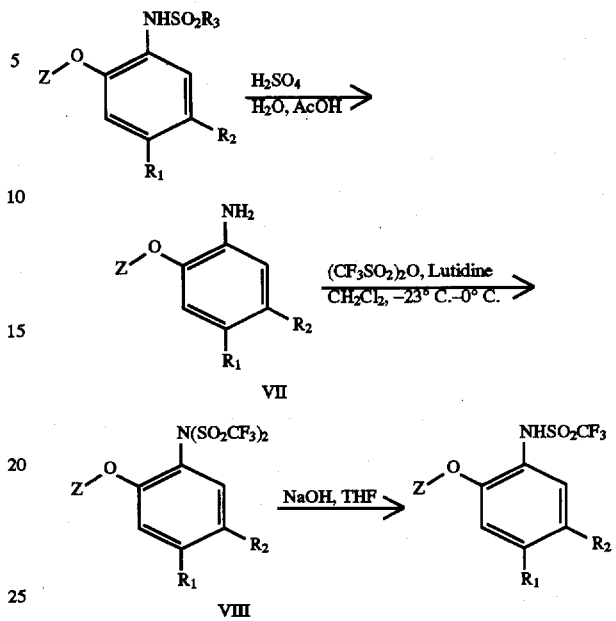

Table 2 depicts structurally certain preferred compounds of the invention. In Table 2, a line crossing through both rings to $R_4$ indicates that the $R_4$ substituent may be present on one or both rings. Furthermore, $R_4$ may be substituted at 0–4 positions which are independently selected from the group consisting of —F, —CN, —Cl, and $CF_3$. $R_5$ is —H or lower alkyl and $R_6$ at each occurrence is independently selected from the group consisting of —H and —$CH_3$. Y represents $NR_5$, O or S.

TABLE 2

| | | | |
|---|---|---|---|
| Z | $R_1$ | $R_2$ | $R_3$ |
| naphthyl (with $R_4$) | $NO_2$, CN, Cl, | H | $C_1$–$C_6$ alkyl $CH_nF_{(3-n)}$ wherein n = 0–3 |
| benzothiazole (with $R_4$) | $CF_3$; or $R_1$ and $R_2$ taken together form | | cyclopentanone |
| benzothiazole isomer (with $R_4$) | | | |
| (with $R_5N$, $R_4$) | | | |

TABLE 2-continued

![structure with NHSO2R3, Z-O, R1, R2]

| Z | R₁ | R₂ | R₃ |
|---|----|----|----|

[structures shown: R₅N/N fused ring-R₄; N/O fused ring-R₄; O/N fused ring-R₄; Y fused ring-R₄; R₆-O/R₆-O benzodioxole-type with R₄]

The foregoing may be better understood by reference to the following examples which are provided for illustration and not intended to limit the scope of the inventive concept. Both below and throughout the specification it is intended that citations to the literature are expressly incorporated by reference.

EXAMPLE 1

N(4-Nitro-2-(naphth-2'-yloxy)phenyl)methanesulfonamide

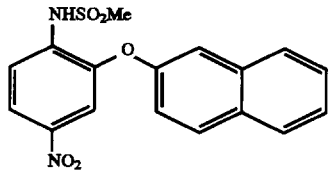

A mixture of 2-bromonaphthalene (0.16 g, 0.77 mmol), N-(2-hydroxy-4-nitrophenyl)methanesulfonamide (0.15 g, 0.65 mmol), potassium carbonate (0.22 g, 1.61 mmol), and copper(I) iodide (0.12 g, 0.65 mmol) in dry DMF (6.5 mL) was stirred at reflux under $N_2$ for 3 hours. The resulting black reaction mixture was partitioned between ethyl acetate and saturated aqueous ammonium chloride. The aqueous layer was separated, and the organic layer was washed (saturated aqueous ammonium chloride, 1x; water, 1x; brine, 1x), dried (MgSO₄), filtered, and evaporated in vacuo. Purification by flash column chromatography (silica gel; 1:1 dichloromethane/hexanes) provided 0.073 g (30%) of the desired product. Recrystallization from ethyl acetate/hexanes gave N-(4-Nitro-2-(naphth-2'-yloxy)phenyl)methanesulfonamide as a colorless solid: mp 167°–168° C.; $^1$H NMR (300 MHz, CDCl₃) δ 3.20 (s, 3H), 7.24 (dd, J=9 Hz, J=2.5 Hz, 1H), 7.44 (s, 1H), 7.47 (d, J=2.5 Hz, 1H), 7.55 (m, 2H), 7.69 (d, J=2.5 Hz, 1H), 7.80 (dd, J=8 Hz, 2.5 Hz, 1H), 7.81 (d, J=9 Hz, 1H), 7.91 (m, 1H), 7.95 (d, J=9 Hz, J=1H), 8.04 (dd, J=9 Hz, J=2.5 Hz, 1H); MS (DCI—NH₃) m/z 376 (M+NH₄)⁺. Anal. Calcd for $C_{17}H_{14}N_2O_5S$: C, 56.27; H, 4.03; N, 7.72.

Found: C, 56.21H, 3.95; N, 7.59.

Preparation of N-(2-hydroxy-4-nitrophenyl)methanesulfonamide:

To a magnetically stirred solution of 2-amino-5-nitrophenol (5.62 g, 36.5 mmol) and chloro-t-butyldimethylsilane (5.00 g, 33.2 mmol) in dry dichloromethane (66 mL) was added triethylamine (5.55 mL, 39.8 mmol) at 25° C. The reaction mixture was stirred at ambient temperature for 4 hours and partitioned between diethyl ether (200 mL) and saturated ammonium chloride. The aqueous layer was separated and the ether layer washed (saturated ammonium chloride, 1x; water, 1x; brine, 1x), dried (MgSO₄), filtered, and evaporated in vacuo. Crystallization from ethyl acetate/hexanes gave 7.5 g (84%) of O-t-butyldimethylsilyl-2-amino-5-nitrophenol O-t-butyldimethylsilyl-2-amino-5-nitrophenol (1.50 g, 5.6 mmol) in dry dimethylformamide (DMF, 5 mL) was added to a suspension of sodium hydride (704 mg; 60% in mineral oil) in dry DMF (11 mL) at 0° C. After the evolution of hydrogen had ended, the orange mixture was stirred at 25° C. for 30 minutes. Methanesulfonyl chloride (0.91 mL, 11.7 mmol) was added drop wisevia a syringe, and the reaction mixture was stirred at 25° C. for 17 hours. The mixture was poured into saturated ammonium chloride (50 mL) and extracted with ethyl acetate (3×100 mL). The combined organic layers were washed (saturated ammonium chloride, 1x; water, 1x; brine, 1x), dried (MgSO₄), filtered, and evaporated in vacuo.. Crystallization from methanol/ethyl acetate/hexanes provided 0.96 g(55%) of N,N-bis (methanesulfonamido)-2-hydroxy-4-nitro- aniline as a colorless solid.

A mixture of N,N-bis(methanesulfonamido)-2-hydroxy-4-nitroaniline (0.90 g, 2.9 mmol) and lithium hydroxide (0.51 g, 12.2 mmol) in 2:1 ethanol:H₂O (15 mL) was stirred at reflux for 17 hours. The reaction mixture was poured into aqueous saturated ammonium chloride and extracted with ethyl acetate (3×100 mL). The combined organic layers were dried(MgSO₄), filtered, and evaporated in vacuo. Crystallization from ethyl acetate-hexanes gave N-(2-hydroxy-4-nitrophenyl)methanesulfonamide as a yellow solid: mp 180°–181.5° C.

EXAMPLE 2

N-(4-Nitro-2-(6'-fluoro-naphth-2'-yloxy)phenyl)methanesulfonamide

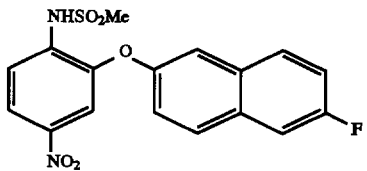

To a solution of 6-fluoro-naphth-2-ol (510 mg, 3.14 mmol) prepared in DMF (20 mL) at room temperature was added N-(4-Nitro-2-bromophenyl)methanesulfonamide (925 mg, 3.51 mmol). The reaction was heated at reflux for 7 hours and cooled to room temperature. The reaction was quenched with 10% aqueous HCl. Celite was added to the two phased solution and the resulting mixture was filtered. The filter cake was washed thoroughly with ethyl acetate. The organic layer was drawn off and the aqueous layer was extracted with ethyl acetate (100 mL, 2x). The combined extracts were diluted with an equal volume of hexanes and the resulting solution washed ($H_2O$, 2x; brine, 2x), dried ($Na_2SO_4$), filtered and concentrated in vacuo to afford a dark brown thick oil that was purified by flash chromatography (silica gel; 20% EtOAc/Hexane) to afford the desired product as a white solid which was recrystallized from acetone/methanol. mp 179°–180° C.; $^1H$ NMR (300 MHz, DMSO-$d_6$) δ 3.20 (s, 3H), 7.44–7.52 (m, 2H), 7.65 (m; 2H), 7.77–7.82 (m; 2H), 7.95–8.10 (m; 3H), 10.25 (br.s., 1H). MS (DCI-$NH_3$) m/z 394 $(M+NH_4)^+$. Analysis Calc'd for $C_{17}H_{13}FN_2O_5S$: C, 54.25; H, 3.48; N, 7.44. Found: C, 54.54; H, 3.28; N, 7.29.

Preparation of 6-fluoro-napth-2-ol:

A flask was charged with 2-fluoro-6-methoxynapthalene (3.80 g, 21.6 mmol) and dichloromethane (86 mL) and cooled to 0° C. in an icebath under a flow of nitrogen. A solution of borontribromide (26 mL of a 1M solution in dichloromethane, 25.9 mmol) was added via cannula. The reaction solution was stirred 15 minutes at 0° C., the cooling bath was removed and the reaction was stirred for 1.5 h at ambient temperature. The reaction was quenched by slowly adding excess 10% aqueous hydrochloric acid. The two-phased reaction mixture was partitioned between ethyl acetate and water. The organic layer was washed (2x, brine), dried ($Na_2SO_4$), filtered and concentrated in vacuo to afford a brown gummy solid. Purification by flash chromatography (silica gel; 20% ethyl acetate/hexane) afforded the desired product (3.63 g, 91% yield). Recrystallization from cold ether/hexanes provided the title compound as a colorless powdery solid. mp 118°–120° C.; 1HNMR (300 MHz, DMSO-$d_6$) δ 7.11–7.18 (m; 2H), 7.30 (td; J=9,3 Hz; 1H), 7.55 (dd; J=10.5,3 Hz; 1H), 7.73–7.79 (m; 2H), 9.73 (s; 1H).

Preparation of 2-fluoro-6-methoxnynapthalene: 2-amino-6-methoxynapthalene (6.84 g, 39.5 mmol) was converted to the corresponding tetrafluoroborate diazonium salt following the procedure of Doyle and Bryker (J. Org. Chem. 1979, 44, 1572–1574) using dichloromethane as the solvent. The resulting diazonium salt was suspended in chlorobenzene (300 mL) and heated to reflux. Nitrogen evolution began prior to reaching reflux and continued after reflux was achieved. When gas evolution ceased the reaction was cooled and diluted with ethyl acetate. The resulting solution was washed (2x, saturated sodium bicarbonate; 2x, brine), dried ($Na_2SO_4$), filtered and concentrated in vacuo to afford a brown oil. Purification by flash chromatography (silica gel; 0.25% Acetone/Hexane) afforded the desired product (4.02 g, 58% yield). 1HNMR (300 MHz, DMSO-$d_6$) δ 3.86 (s, 3H), 7.22 (dd; J=9, 3 Hz; 1H), 7.35 (dd; J=9,3 Hz; 1H), 7.39 (dd; J=7.5,3 Hz; 1H), 7.63(dd; J=10.5,3 Hz; 1H), 7.82 (d; J=10 Hz; 1H), 7.89 (dd; J=10,6 Hz; 1H).

Preparation of 2-amino-6-methoxynapthalene:

A 2-necked 100 mL round bottom flask was charged with commercially available 2-acetyl-6-methoxynapthalene(5.0 g, 25 mmol) and trifluoroacetic acid (500 mmol, 38 mL) and fitted with a reflux condenser and a stopper. The solution was heated to 120° C. and sodium azide (3.25 g, 50 mml) was added over 30 minutes. Each addition resulted in a visible exotherm. Gas evolution ceased 30 minutes after complete addition of the azide. The reaction was cooled and poured into excess saturated aqueous sodium bicarbonate. The resulting mixture was extracted (2x, ethyl acetate). The combined organic extracts were washed (2x, brine), dried ($Na_2SO_4$), filtered and concentrated in vacuo to afford a light red solid which was a mixture (~5:1) of the respective N-acetyl-6-methoxynapthylamine and N-methylaminocarbonyl-6-methoxynapthalene. The mixture was carried on without purification. The unpurified solid (4.51 g, 20.9 mmol) was dissolved in hot ethanol (100 mL). Water (15 mL) and concentrated sulfuric acid (2.24 g, 41.9 mmol) were added and the reaction heated at reflux for 24 h during which time a thick precipitate formed. The reaction was cooled to 0° C. and the solid 2-amino-6-methoxynapthalene hydrogen sulfate salt was collected by filtration. The salt was neutralized by partitioning between aqueous sodium hydroxide(15.8 g, 0.396 mmol in 200 mL of water) and ethyl acetate. The layers were separated and the aqueous layer extracted with ethyl acetate (2x). The organic layers were combined, washed (brine, 3x), dried ($Na_2SO_4$), filtered and concentrated in vacuo to afford a purple solid. Recrystallization from ethyl acetate and acetone gave the title compound in three fractions (2.64 g, 61%) as a light beige solid. mp 133°–136° C.

Preparation of N-(4-Nitro-2-bromophenyl)methanesulfonamide:

Commercially available 2-bromo-4-nitroaniline (10.0 g, 46.07 mmol) was dissolved in DMF (250 mL) and NaH (60% in oil dispersion; 3.7 g, 92.15 mmol) added portion wise at 0° C. After 15 minutes, methanesulfonyl chloride (10.7 mL, 138.23 mmol) was added and the reaction was stirred overnight at ambient temperature. The reaction was quenched with 1M citric acid (100 mL) and extracted with ethyl acetate (3x). The combined extracts were washed with brine (2x), dried ($MgSO_4$), filtered and concentrated in vacuo to yield a red oil that was purified by flash chromatography (silica gel; 20% EtOAc/Hexane) to afford the title compound as a yellow solid which was recrystallyzed from ether/hexanes. mp 148°–151° C.; $^1H$ NMR (300 MHz, DMSO-$d_6$) δ 3.24 (s, 3H), 7.70 (d; J=9 Hz; 1H), 8.23 (dd; J=9,3 Hz; 1H), 8.49 (d; J=3 Hz; 1H), 9.85 (br. s., 1H). MS (DCI-$NH_3$) m/z 312 $(M+NH_4)^+$.

EXAMPLE 3

N-(4-Nitro-2-(benzothiophen-5'-yloxy)phenyl)methanesulfonamide

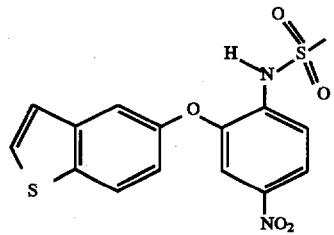

To a solution of 5-hydroxythiophene (1.9 g, 12.66 mmol; prepared by the method of Zambias, R. and Hammond, M., Syn. Commun., 21(7): 959–964, (1991)) and $K_2CO_3$ (9.3 g, 67.52 mmol) in DMF (50 mL) at room temperature was added CuCl (1.67 g, 16.88 mmol). The reaction was stirred for 20 minutes after which N-(4-nitro-2-bromophenyl)methanesulfonamide (2.49 g, 8.44 mmol) prepared as in Example 2 was added. The reaction was heated at reflux for 7 hours and allowed to cool to room temperature. The reaction was acidified with 1N HCl (aq) and extracted into EtOAc (3X). The combined extracts were washed with brine (2X), dried (MgSO$_4$), filtered and concentrated in vacuo to afford a brown oil that was purified by flash chromatography (silica gel; 20% EtOAc/Hexane) and recrystallized from ethyl acetate/hexanes to afford the desired product. mp 171°–173° C.; $^1$H NMR (300 MHz, DMSO-d$_6$) δ 3.11 (s, 3H), 7.22 (dd; J=9, 3 Hz; 1H), 7.44 (d; J=6 Hz; 1H), 7.54 (d; J=3 Hz; 1H), 7.68 (d; J=3 Hz; 1H), 7.75 (d; J=9 Hz; 1H), 7.89 (d; J=6 Hz; 1H), 8.05 (dd; J=9,3 Hz; 1H), 8.12 (d; J=9 Hz; 1H), 10.21 (bs; 1H). MS (DCI-NH$_3$) m/z 382 (M+NH$_4$)$^+$ and 364 (M+NH$_4$—H$_2$O)$^+$. Analysis calc'd for C$_{15}$H$_{12}$N$_2$O$_5$S$_2$: C, 49.44; H, 3.32; N, 7.69. Found: C, 49.08; H, 3.27; N, 7.52.

EXAMPLE 4

N-4-Nitro-2-(benzothiazol-6'-yloxy)phenyl) methanesulfonamide

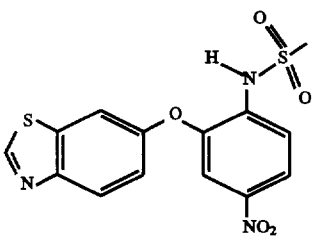

Following the procedure in Example 3, 6-hydroxybenzothiazole (1.0 g, 6.61 mmol) was converted to the title compound and purified by flash chromatography (silica gel; 20% EtOAc/Hexane) and recrystallized from ethyl acetate/hexanes. mp 182°–184° C.; $^1$H NMR (300 MHz, DMSO-d$_6$) δ 3.2 (s, 3H), 7.39 (dd; J=9,3 Hz; 1H), 7.63 (d; J=3 Hz; 1H), 7.76 (d; J=9 Hz; 1H), 7.96 (d; J=3 Hz; 1H), 8.06 (dd; J=9,3 Hz; 1H), 8.18 (d; J=9 Hz; 1H, 9.39 (s, 1H), 10.21 (bs; 1H). MS (DCI-NH$_3$) m/z 383 (M+NH$_4$)$^+$ and 366 (M+H)$^+$. Analysis calc'd for C$_{14}$H$_{11}$N$_3$O$_5$S$_2$: C, 46.02; H, 3.03; N, 11.5. Found: C 46.03; H, 2.97; N, 11.28.

EXAMPLE 5

N-(4-Nitro-2-(1,3-benzodioxol-6-yloxy)phenyl) methanesulfonamide

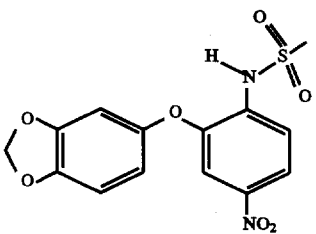

The title compound was prepared following the procedure in Example 1, but employing 4-bromo-1,2-methylenedioxybenzene (0.74 g, 3.19 mmol) in lieu of 2-bromonaphthalene. Purification by flash chromatography (silica gel; 30% EtOAc/Hexane) and recrystallization from ethyl acetate/hexanes provided N-(4-Nitro-2-(1,2-methylenedioxy phen-4-yl) phenyl)methanesulfonamide. mp 146°–146.5° C.; $^1$H NMR (300 MHz, DMSO-d$_6$) δ 3.2 (s, 3H), 6.14 (s, 2H), 6.63 (dd; J=9,3 Hz; 1H), 6.82 (d; J=3 Hz; 1H )7.00 (d; J=9 Hz; 1H), 7.47 (d; J=3 Hz; 1H), 7.69 (d; J=9 Hz; 1H), 7.98 (dd; J=9,3 Hz; 1H), 10.07 (s, 1H). MS (DCI-NH$_3$) m/z 370 (M+NH$_4$)$^+$. Analysis calc'd for C$_{14}$H$_{12}$N$_2$O$_7$S: C, 47.73; H, 3.43; N, 7.95. Found: C, 47.80; H, 3.35; N, 7.91.

EXAMPLE 6

N-(2-(naphth-2-yloxy)-4-nitrophenyl) trifluoromethanesulfonamide

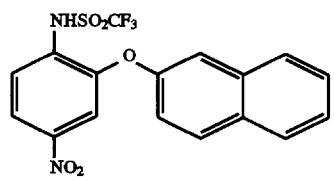

To a solution of N-(2-(naphth-2-yloxy)-4-nitrophenyl)-N, N-bis(trifluoromethanesulfonyl)amine (o.428 g, 0.79 mmol) in THF (10 mL) was added excess aqueous sodium hydroxide (2 mL, 10% aqueous NaOH). The resulting solution was stirred for 10 minutes at ambient temperature and quenched by adding excess 10% aqueous HCl. The two phased solution was partitioned between ethyl acetate and water. The organic layer was washed (2x, brine) dried (Na$_2$SO$_4$), filtered and concentrated in vacuo. Recrystallization from ether/hexanes afforded the title compound. mp 117–120° C.; 1HNMR (300 MHz, CDCl$_3$) δ 7.21(dd; J=9.3 Hz; 1H), 7.53 (d; J=2.5 Hz; 1H), 7.56–7.59 (m; 2H), 7.64 (d; J=2.5 Hz; 1H), 7.83 (d; J=9 Hz; 1H), 7.86–8.03 (m=3H); Anal. Calcd for C$_{17}$H$_{11}$N$_2$O$_5$F$_3$S: C, 49.52; H, 2.69; N, 6.79. Found: C, 49.52; H, 2.69; N, 6.75.

Preparation of N-(2-(naphth-2-yloxy)-4-nitrophenyl)-N,N bis(trifluoromethanesulfonyl)amine:

A solution of 2-(napth-2-yloxy)-4-nitroaniline (300 mg, 1.07 mmol) and lutidine (0.1145 g, 1.07 mmol) in dry CH$_2$Cl$_2$ (25 mL) was cooled to –23° C. To the solution was added trifluromethanesulfonic anhydride (0.604 g, 2.14 mmol). The reaction was stirred for 0.15 h at –23° C., the cooling bath was removed, the reaction warmed to 0° C. and quenched by adding excess water. The two-phased solution was partitioned between ethyl acetate and brine. The organic layer was washed (1x, 10% aqueous HCl; 1x, saturated aqueous NaHCO$_3$; 1x, brine), dried (Na$_2$SO$_4$), filtered and concentrated in vacuo. Purification by flash chromatography (silica gel; 25% ethyl acetate/hexane) afforded the compound N-(2-(napth-2-yloxy)-4-nitrophenyl)-N,N bis (trifluoromethanesulfonyl)amine.

Preparation of 2-(napth-2-yloxy)-4-nitroaniline:

A solution of N-(2-(napth-2-yloxy)-4-nitrophenyl]) methanesulfonamide (0.17 g, 0.474 mmol) in acetic acid(4 mL), water (1 mL), and concentrated sulfuric acid (3 mL) was refluxed for 3 h, cooled, and neutralized by pouring into a saturated aqueous solution of sodium carbonate. The resulting mixture was extracted (2x, ethyl acetate). The combined organic extracts were washed (2x, brine), dried (Na$_2$SO$_4$), filtered and concentrated in vacuo to afford a brown glassy film. Purification by flash chromatography (silica gel; 15% ethyl acetate/hexane) afforded the compound 2-(napth-2-yloxy)-4-nitroaniline. $^1$HNMR (300 MHz, CDCl$_3$) δ 4.63(s, 2H), 6.82 (d, J=9 Hz; 1H), 7.24 (dd; J=9,3 Hz; 1H), 7.36 (d; J=2.5 Hz; 1H), 7.46 (pd; J=7.5,7.5, 7.5,7.5,2.5 Hz; 2H), 7.73 (d; J=7.5 Hz; 1H), 7.7 (s; 1H), 7.83 (br d; J=7.5 Hz; 1H), 7.87 (d; J=9 Hz; 1H), 7.95 (dd; J=9,3 Hz; 1H), 8.04.

EXAMPLE 7

N-(2-(6-fluoronaphthal-2-yloxy)-4-nitrophinyl) trifluoromethanesulfnamide

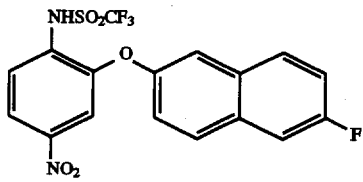

The title compound was prepared following the procedure described in Example 6, but employing N-(2-(6-fluoronaphth-2-yloxy)-4-nitrophenyl) trifluoromethanesulfnamide in lieu of N-(2-(naphth-2-yloxy)-4-nitrophenyl)trifluoromethanesulfnamide.

We claim:

1. A compound having the formula:

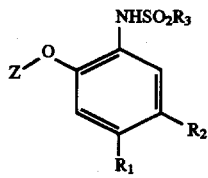

I wherein

Z is selected from the group consisting of:
   (a) benzthiazol-5-yl;
   (b) substituted benzthiazol-5-yl wherein the hydrogen atom attached to one to four of the carbon atoms is replaced with a substituent independently selected from $R_4$ wherein $R_4$ is —F, —CN, —Cl, or —CF$_3$;
   (c) benzthiazol-6-yl;
   (d) substituted benzthiazol-6-yl wherein the hydrogen atom attached to one to four of the carbon atoms is replaced with a substituent independently selected from $R_4$ wherein $R_4$ is as defined above;
   (e) benzoxazol-5-yl;
   (f) substituted benzoxazol-5-yl wherein the hydrogen atom attached to one to four of the carbon atoms is replaced with a substituent independently selected from $R_4$ wherein $R_4$ is as defined above;
   (g) benzoxazol-6-yl;
   (h) substituted benzoxazol-6-yl wherein the hydrogen atom attached to one to four of the carbon atoms is replaced with a substituent independently selected from $R_4$ wherein $R_4$ is as defined above;
   (i) benzthiophen-5-yl;
   (k) substituted benzthiophen-5-yl wherein the hydrogen atom attached to one to four of the carbon atoms is replaced with a substituent independently selected from $R_4$ wherein $R_4$ is as defined above;
   (l) benzthiophen-6-yl;
   (m) substituted benzthiophen-6-yl wherein the hydrogen atom attached to one to four of the carbon atoms is replaced with a substituent independently selected from $R_4$ wherein $R_4$ is as defined above;
   (n) benzimidazol-5-yl wherein the hydrogen atom attached to the nitrogen atom is optionally substituted with lower alkyl;
   (o) substituted benzimidazol-5-yl wherein the hydrogen atom attached to the nitrogen atom is optionally substituted with lower alkyl and the hydrogen atom attached to one to four of the carbon atoms is replaced with a substituent independently selected from $R_4$ wherein $R_4$ is as defined above;
   (p) benzimidazol-6-yl wherein the hydrogen atom attached to the nitrogen atom is optionally substituted with lower alkyl;
   (q) substituted benzimidazol-6-yl wherein the hydrogen atom attached to the nitrogen atom is optionally substituted with lower alkyl and the hydrogen atom attached to one to four of the carbon ring atoms is replaced with a substituent independently selected from $R_4$ wherein $R_4$ is as defined above;
   (r) 1,3-benzodioxol-5-yl;
   (s) substituted 1,3-benzodioxol-5-yl wherein the hydrogen atom attached to one or two of the carbon ring atoms is replaced with a substituent independently selected from $R_4$ wherein $R_4$ is as defined above;
   (t) benzofur-5-yl;
   (u) substituted benzofur-5-yl wherein the hydrogen atom attached to one to four of the carbon ring atoms is replaced with a substituent independently selected from $R_4$ wherein $R_4$ is as defined above;
   (v) benzofur-6-yl;
   (w) substituted benzofur-6-yl wherein the hydrogen atom attached to one to four of the carbon ring atoms is replaced with a substituent independently selected from $R_4$ wherein $R_4$ is as defined above;
   (x) indol-5-yl wherein the hydrogen atom attached to the nitrogen atom is optionally substituted with lower alkyl;
   (y) substituted indol-5-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;
   (z) indol-6-yl wherein the hydrogen atom attached to the nitrogen atom is optionally substituted with lower alkyl; and
   (aa) substituted indol-6-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;

$R_1$ is selected from the group consisting of —NO$_2$, —CN, —Cl, and CF$_3$;

$R_2$ is —H or $R_1$ and $R_2$ taken together with the atoms to which they are attached define a 5-, 6- or 7-membered saturated carbocyclic or saturated heterocyclic ring having a single heteroatom which is oxygen, nitrogen or sulfur wherein the carbocyclic or heterocyclic ring is unsubstituted or substituted with one or two substituents selected from the group consisting of oxo, alkyl and hydroxy; and $R_3$ is selected from the group consisting of lower alkyl and CH$_n$F$_{(3-n)}$ wherein n is 0, 1, 2 or 3;

or a pharmaceutically acceptable salt or prodrug thereof.

2. The compound according to claim 1 wherein Z is as defined therein, $R_1$ is —NO$_2$, $R_2$ is H, and $R_3$ is CH$_3$ or a pharmaceutically acceptable salt or prodrug thereof.

3. The compound according to claim 1 wherein Z is (a) benzthiazol-6-yl; (b) substituted benzthiazol-6-yl wherein the hydrogen atom attached to one to four of the carbon atoms is replaced with a substituent independently selected from $R_4$ wherein $R_4$ is as defined therein; (c) benzthiophen-5-yl; (d) substituted benzthiophen-5-yl wherein the hydrogen atom attached to one to four of the carbon atoms is replaced with a substituent independently selected from $R_4$ wherein $R_4$ is as defined therein; (e) 1,3-benzodioxol-6-yl; (f) substituted 1,3-benzodioxol-6-yl wherein the hydrogen atom attached to one or two of the carbon atoms is replaced with a substituent independently selected from $R_4$ wherein $R_4$ is as defined therein; $R_1$ is —$NO_2$, $R_2$ is —H; and $R_3$ is —$CH_3$ or a pharmaceutically acceptable salt or prodrug thereof.

4. A compound selected from the group consisting of

N-(4-Nitro-2-(benzothiophen-5'-yloxy)phenyl) methanesulfonamide;

N-(4-Nitro-2-(benzothiazol-6'-yloxy)phenyl) methanesulfonamide;

N-(4-Nitro-2-(1,3-benzodioxol-5'-yloxy)phenyl) methanesulfonamide or a pharmaceutically acceptable salt or prodrug thereof.

5. A pharmaceutical composition comprising a pharmaceutically acceptable carrier and a therapeutically effective amount of a compound having the formula:

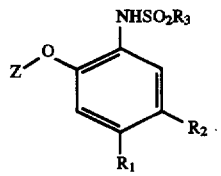

wherein

Z is selected from the group consisting of:

(a) benzthiazol-5-yl;

(b) substituted benzthiazol-5-yl wherein the hydrogen atom attached to one to four of the carbon atoms is replaced with a substituent independently selected from $R_4$ wherein $R_4$ is —F, —CN, —Cl, or —$CF_3$;

(c) benzthiazol-6-yl;

(d) substituted benzthiazol-6-yl wherein the hydrogen atom attached to one to four of the carbon atoms is replaced with a substituent independently selected from $R_4$ wherein $R_4$ is as defined above;

(e) benzoxazol-5-yl;

(f) substituted benzoxazol-5-yl wherein the hydrogen atom attached to one to four of the carbon atoms is replaced with a substituent independently selected from $R_4$ wherein $R_4$ is as defined above;

(g) benzoxazol-6-yl;

(h) substituted benzoxazol-6-yl wherein the hydrogen atom attached to one to four of the carbon atoms is replaced with a substituent independently selected from $R_4$ wherein $R_4$ is as defined above;

(i) benzthiophen-5-yl;

(k) substituted benzthiophen-5-yl wherein the hydrogen atom attached to one to four of the carbon atoms is replaced with a substituent independently selected from $R_4$ wherein $R_4$ is as defined above;

(l) benzthiophen-6-yl;

(m) substituted benzthiophen-6-yl wherein the hydrogen atom attached to one to four of the carbon atoms is replaced with a substituent independently selected from $R_4$ wherein $R_4$ is as defined above;

(n) benzimidazol -5-yl wherein the hydrogen atom attached to the nitrogen atom is optionally substituted with lower alkyl;

(o) substituted benzimidazol-5-yl wherein the hydrogen atom attached to the nitrogen atom is optionally substituted with lower alkyl and the hydrogen atom attached to one to four of the carbon atoms is replaced with a substituent independently selected from $R_4$ wherein $R_4$ is as defined above;

(p) benzimidazol-6-yl wherein the hydrogen atom attached to the nitrogen atom is optionally substituted with lower alkyl;

(q) substituted benzimidazol-6-yl wherein the hydrogen atom attached to the nitrogen atom is optionally substituted with lower alkyl and the hydrogen atom attached to one to four of the carbon ring atoms is replaced with a substituent independently selected from $R_4$ wherein $R_4$ is as defined above;

(r) 1,3-benzodioxol-5-yl;

(s) substituted 1,3-benzodioxol-5-yl wherein the hydrogen atom attached to one or two of the carbon ring atoms is replaced with a substituent independently selected from $R_4$ wherein $R_4$ is as defined above;

(t) benzofur-5-yl;

(u) substituted benzofur-5-yl wherein the hydrogen atom attached to one to four of the carbon ring atoms is replaced with a substituent independently selected from $R_4$ wherein $R_4$ is as defined above;

(v) benzofur-6-yl;

(w) substituted benzofur-6-yl wherein the hydrogen atom attached to one to four of the carbon ring atoms is replaced with a substituent independently selected from $R_4$ wherein $R_4$ is as defined above;

(x) indol-5-yl wherein the hydrogen atom attached to the nitrogen atom is optionally substituted with lower alkyl;

(y) substituted indol-5-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;

(z) indol-6-yl wherein the hydrogen atom attached to the nitrogen atom is optionally substituted with lower alkyl; and (aa) substituted indol-6-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;

$R_1$ is selected from the group consisting of —$NO_2$, —CN, —Cl and $CF_3$;

$R_2$ is —H or $R_1$ and $R_2$ taken together with the atoms to which they are attached define a 5-, 6- or 7-membered saturated carbocyclic or saturated heterocyclic ring having a single heteroatom which is oxygen, nitrogen or sulfur wherein the carbocyclic or heterocyclic ring is unsubstituted or substituted with one or two substituents selected from the group consisting of oxo, alkyl and hydroxy; and $R_3$ is selected from the group consisting of lower alkyl and $CH_n F_{(3-n)}$ wherein n is 0, 1, 2 or 3;

or a pharmaceutically acceptable salt or prodrug thereof.

6. A pharmaceutical composition of claim 5 wherein Z is as defined therein, $R_1$ is —$NO_2$, $R_2$ is H, and $R_3$ is $CH_3$.

7. A pharmaceutical composition comprising a pharmaceutically acceptable carrier and a therapeutically effective amount of a compound selected from the group consisting of N-(4-Nitro-2-(benzothiophen-5'-yloxy)phenyl) methanesulfonamide;

N-(4-Nitro-2-(benzothiazol-6'-yloxy)phenyl) methanesulfonamide;

N-(4-Nitro-2-(1,3-benzodioxol-5'-yloxy)phenyl) methanesulfonamide or a pharmaceutically acceptable salt or prodrug thereof.

8. A method for inhibiting prostaglandin synthesis comprising administering to a mammal in need of such treatment a therapeutically effective amount of a compound having the formula:

wherein

Z is selected from the group consisting of:
(a) benzthiazol-5-yl;
(b) substituted benzthiazol-5-yl wherein the hydrogen atom attached to one to four of the carbon atoms is replaced with a substituent independently selected from $R_4$ wherein $R_4$ is —F, —CN, —Cl, or —$CF_3$;
(c) benzthiazol-6-yl;
(d) substituted benzthiazol-6-yl wherein the hydrogen atom attached to one to four of the carbon atoms is replaced with a substituent independently selected from $R_4$ wherein $R_4$ is as defined above;
(e) benzoxazol-5-yl;
(f) substituted benzoxazol-5-yl wherein the hydrogen atom attached to one to four of the carbon atoms is replaced with a substituent independently selected from $R_4$ wherein $R_4$ is as defined above;
(g) benzoxazol-6-yl;
(h) substituted benzoxazol-6-yl wherein the hydrogen atom attached to one to four of the carbon atoms is replaced with a substituent independently selected from $R_4$ wherein $R_4$ is as defined above;
(i) benzthiophen-6-yl;
(k) substituted benzthiophen-5-yl wherein the hydrogen atom attached to one to four of the carbon atoms is replaced with a substituent independently selected from $R_4$ wherein $R_4$ is as defined above;
(l) benzthiophen-6-yl;
(m) substituted benzthiophen-6-yl wherein the hydrogen atom attached to one to four of tho carbon atoms is replaced with a substituent independently selected from $R_4$ wherein $R_4$ is as defined above;
(n) benzimidazol-5-yl wherein the hydrogen atom attached to the nitrogen atom is optionally substituted with lower alkyl;
(o) substituted benzimidazol-5-yl wherein the hydrogen atom attached to the nitrogen atom is optionally substituted with lower alkyl and the hydrogen atom attached to one to four of the carbon atoms is replaced with a substituent independently selected from $R_4$ wherein $R_4$ is as defined above;
(p) benzimidazol-6-yl wherein the hydrogen atom attached to the nitrogen atom is optionally substituted with lower alkyl;
(q) substituted benzimidazol-6-yl wherein the hydrogen atom attached to the nitrogen atom is optionally substituted with lower alkyl and the hydrogen atom attached to one to four of the carbon ring atoms is replaced with a substituent independently selected from $R_4$ wherein $R_4$ is as defined above;
(r) 1,3-benzodioxol-5-yl;
(s) substituted 1,3-benzodioxol-5-yl wherein the hydrogen atom attached to one or two of the carbon ring atoms is replaced with a substituent independently selected from $R_4$ wherein $R_4$ is as defined above;
(t) benzofur-5-yl;
(u) substituted benzofur-5-yl wherein the hydrogen atom attached to one to four of the carbon ring atoms is replaced with a substituent independently selected from $R_4$ wherein $R_4$ is as defined above;
(v) benzofur-6-yl;
(w) substituted benzofur-6-yl wherein the hydrogen atom attached to one to four of the carbon ring atoms is replaced with a substituent independently selected from $R_4$ wherein $R_4$ is as defined above;
(x) indol-5-yl wherein the hydrogen atom attached to the nitrogen atom is optionally substituted with lower alkyl;
(y) substituted indol-5-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;
(z) indol-6-yl wherein the hydrogen atom attached to the nitrogen atom is optionally substituted with lower alkyl; and
(aa) substituted indol-6-yl wherein the hydrogen atom attached to the nitrogen atom is optionally substituted with lower alkyl and wherein the hydrogen atom attached to one to four of the carbon ring atoms is replaced with a substituent independently selected from $R_4$ wherein $R_4$ is as defined above;

$R_1$ is selected from the group consisting of —$NO_2$, —CN, —Cl, and $CF_3$;

$R_2$ is —H or $R_1$ and $R_2$ taken together with the atoms to which they are attached define a 5-, 6- or 7-membered saturated carbocyclic or saturated heterocyclic ring having a single heteroatom which is oxygen, nitrogen or sulfur wherein the carbocyclic or heterocyclic ring is unsubstituted or substituted with one or two substituents selected from the group consisting of oxo, alkyl and hydroxy; and $R_3$ is selected from the group consisting of lower alkyl and $CH_nF_{(3-n)}$ wherein n is 0, 1, 2 or 3;

or a pharmaceutically acceptable salt or prodrug thereof.

9. A method of claim 8 wherein Z is as defined therein, $R_1$ is —$NO_2$, $R_2$ is H, and $R_3$ is $CH_3$.

10. A method for inhibiting prostaglandin synthesis comprising administering to a mammal in need of such treatment a therapeutically effective amount of a compound selected from the group consisting of N-(4-Nitro-2-(benzothiophen-5'-yloxy)phenyl) methanesulfonamide;

N-(4-Nitro-2-benzothiazol-6'-yloxy)phenyl) methanesulfonamide;

N-(4-Nitro-2-(1,3-benzodioxol-5'-yloxy)phenyl) methanesulfonamide or a pharmaceutically acceptable salt or prodrug thereof.

* * * * *